United States Patent
Hoffman et al.

(10) Patent No.: US 11,364,053 B2
(45) Date of Patent: Jun. 21, 2022

(54) TIBIOPEDAL VASCULAR CLOSURE BAND

(71) Applicant: Terumo Medical Corporation, Somerset, NJ (US)

(72) Inventors: Brian Hoffman, Princeton, NJ (US); Kendra Krentz, Wilmington, DE (US)

(73) Assignee: Terumo Medical Corporation, Somerset, NJ (US)

( * ) Notice: Subject to any disclaimer, the term of this patent is extended or adjusted under 35 U.S.C. 154(b) by 72 days.

(21) Appl. No.: 16/442,009

(22) Filed: Jun. 14, 2019

(65) Prior Publication Data

US 2020/0390469 A1     Dec. 17, 2020

(51) Int. Cl.
*A61B 17/54*        (2006.01)
*A61B 17/135*      (2006.01)
*A61B 17/00*        (2006.01)

(52) U.S. Cl.
CPC ............ *A61B 17/54* (2013.01); *A61B 17/135* (2013.01); *A61B 2017/00022* (2013.01); *A61B 2017/00907* (2013.01)

(58) Field of Classification Search
CPC ... A61B 17/132; A61B 17/12; A61B 17/1325; A61B 17/135; A61B 17/54; A61B 2017/00022; A61B 2017/00907; A61F 5/34; A61F 13/00; A61F 13/06
See application file for complete search history.

(56) References Cited

U.S. PATENT DOCUMENTS

| | | | |
|---|---|---|---|
| 7,498,477 B2 | 3/2009 | Wada et al. | |
| 9,033,906 B2 | 5/2015 | Nolan et al. | |
| 2007/0161933 A1 | 7/2007 | Ravikumar | |
| 2012/0022422 A1 | 1/2012 | Ravikumar | |
| 2013/0085428 A1 | 4/2013 | Deshpande | |
| 2013/0245674 A1* | 9/2013 | Wada | A61B 17/135 606/202 |
| 2014/0276256 A1* | 9/2014 | Raniere | A61F 5/012 601/18 |

(Continued)

FOREIGN PATENT DOCUMENTS

| | | |
|---|---|---|
| WO | 2016112342 A1 | 7/2016 |
| WO | 2017165108 A1 | 9/2017 |
| WO | 2017210596 A1 | 12/2017 |

OTHER PUBLICATIONS

International Search Report and Written Opinion of the International Searching Authority from corresponding PCT Application No. PCT/US2020/036067, dated Sep. 16, 2020 (13 pages).

*Primary Examiner* — George J Ulsh
(74) *Attorney, Agent, or Firm* — Quarles & Brady LLP; James J Aquilina

(57) ABSTRACT

The present application discloses a hemostatic device comprising a flexible, adjustable closure device that is adapted to fit the lower leg and foot of patients having a range of anatomical differences in leg and foot shape and size, the hemostatic device further comprising at least one compression element that is adapted to apply targeted pressure to a surgical vascular access site located on the patient's lower leg or foot. In some embodiments, the compression element is moveable such that it may be used to apply pressure to a select one of common arterial access points located on the lower leg or foot.

20 Claims, 9 Drawing Sheets

(56) References Cited

U.S. PATENT DOCUMENTS

| | | | |
|---|---|---|---|
| 2015/0245975 A1* | 9/2015 | Ravikumar | A61H 1/008 |
| | | | 601/152 |
| 2016/0206325 A1 | 7/2016 | Ward et al. | |
| 2016/0235578 A1* | 8/2016 | Romo | A61F 5/0195 |
| 2017/0128306 A1* | 5/2017 | Chase | A61F 13/062 |
| 2017/0333281 A1* | 11/2017 | Frank | A61H 9/0078 |
| 2018/0000651 A1* | 1/2018 | Pan | A61F 13/06 |
| 2019/0133871 A1* | 5/2019 | Chase | A61H 9/0078 |

\* cited by examiner

TIBIOPEDAL VASCULAR CLOSURE BAND

BACKGROUND

The present invention relates to a closure band adapted to act as a compression device to promote hemostasis at a surgical access site, and more particularly to a vascular closure band adapted specifically for use on the lower leg and foot of a patient.

After a surgical procedure involving arterial or venous access, it may be desirable or necessary to apply pressure to the access site to promote hemostasis. Existing closure bands—some of which are in an annular shape—have been used in the past to apply pressure to the access site, regardless of the location of the access site on the body. When used on some portions of the body—for example the lower leg and/or foot—such bands may tend to migrate, thus reducing the compressive effectiveness of the device.

Accordingly, there is a need for a vascular closure band that addresses these and other drawbacks of the prior art.

SUMMARY OF THE DISCLOSURE

In one respect, the present disclosure comprises a closure device adapted to simultaneously fit around at least a portion of a lower leg and at least a portion of a foot of a patient, the closure device comprising at least one compression element adapted to apply targeted pressure to at least one artery or vein located in at least one of the lower leg and foot.

In another respect, the present disclosure comprises a hemostatic device comprising a flexible element adapted to be wrapped and releasably secured around at least a portion of a lower leg and at least a portion of a foot of a patient; and at least one compression element adapted to apply targeted pressure to at least one artery or vein located in at least one of the lower leg and foot, the at least one compression element being fixedly attached or removably attachable to the flexible element.

In yet another respect, the present disclosure comprises a method of forming a closure device, the method comprising forming the closure device with a first portion that is adapted to be wrapped and releasably secured around at least a portion of a lower leg of a patient; forming the closure device with a second portion that is adapted to be wrapped and releasably secured around at least a portion of a foot of the patient; providing the closure device with at least one attachment element, the at least one attachment element adapted for either fixed or removeable attachment of at least one compression element thereto, the at least one compression element adapted to apply targeted pressure to at least one artery or vein located in at least one of the lower leg and foot.

BRIEF DESCRIPTION OF THE DRAWINGS

The present disclosure will hereinafter be described in conjunction with the appended drawing figures, wherein like numerals denote like elements.

DETAILED DESCRIPTION OF THE EMBODIMENT(S)

Figure 1:
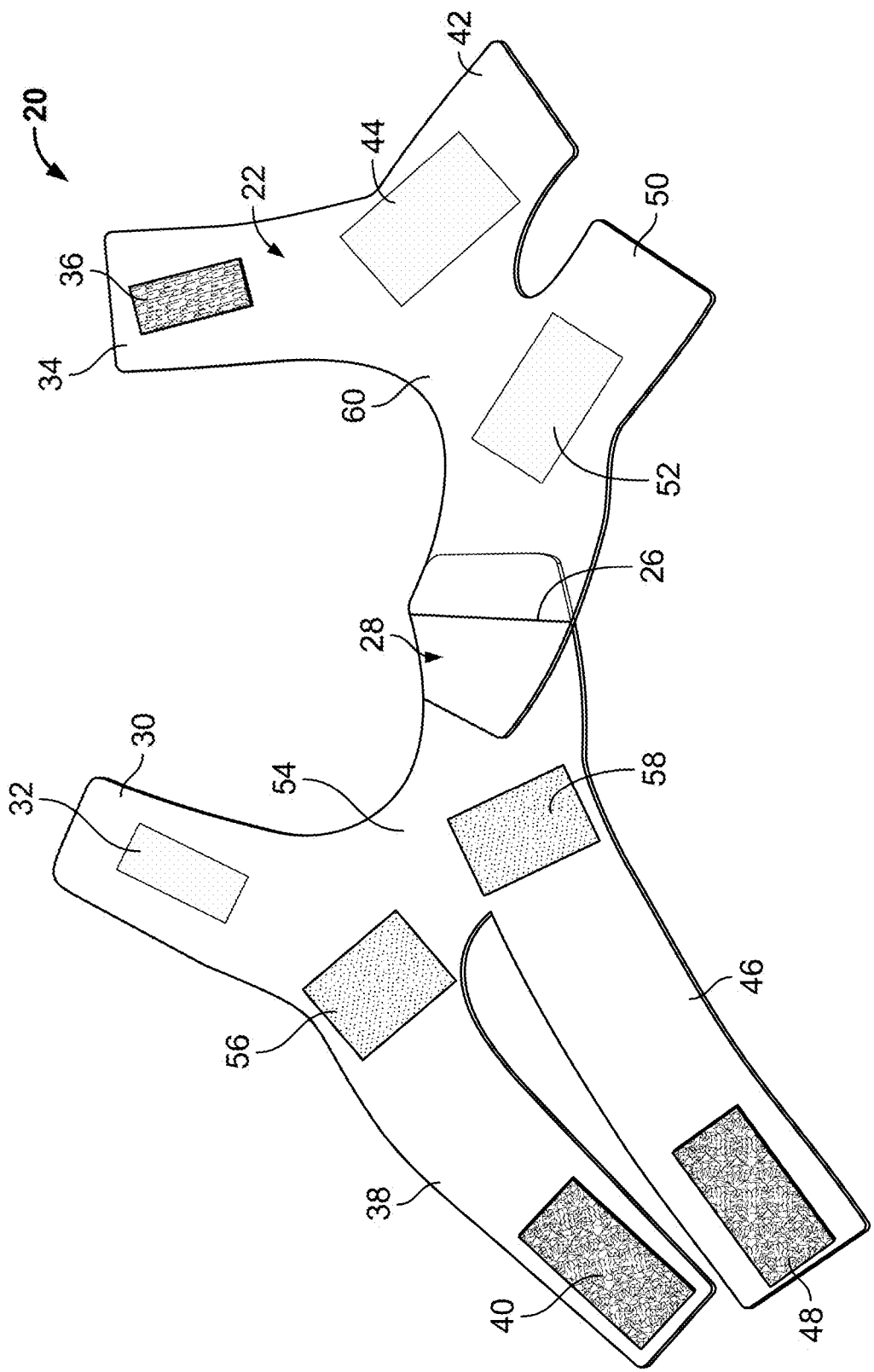
FIG. 1 is a front perspective view of a closure band according to an embodiment of the present disclosure, in an unwrapped configuration.

The ensuing detailed description provides exemplary embodiment(s) only, and is not intended to limit the scope, applicability, or configuration thereof. Rather, the ensuing detailed description of the exemplary embodiment(s) will provide those skilled in the art with an enabling description for implementing these embodiment(s). It should be understood that various changes may be made in the function and arrangement of elements of the embodiment(s) without departing from the spirit and scope of the invention, as set forth in the appended claims.

Directional terms (e.g., upper, lower, left, right, etc.) may be used herein. These directional terms are merely intended to assist in disclosing the embodiment(s) and claiming the invention and are not intended to limit the claimed invention in any way. In addition, reference numerals that are introduced in the specification in association with a drawing figure may be repeated in one or more subsequent figure(s) without additional description in the specification, in order to provide context for other features.

For purposes of the present specification and claims, the term "ankle" should be understood to form a portion of a patient's "lower leg."

For purposes of the present specification and claims, the term "targeted pressure" should be understood to refer to a force that is distributed over a defined area, the force being directed in a direction that is substantially towards a center of a respective body part and having a value that substantially exceeds the value of the standard forces being applied to the remainder of the respective body part via the closure device.

The increased prevalence of Peripheral Arterial Disease (PAD) in patients has led to an accompanying increase in the need for peripheral interventions to attempt to clear occlusions from or surgically introduce stents into vascular pathways. When antegrade crossing fails, vascular access is commonly achieved through a retrograde approach, upwardly from below the patient's knee. The three primary arterial access sites for a retrograde approach are the Dorsalis Pedis (DP), Anterior Tibial (AT), and Posterior Tibial (PT) arteries. Vascular access is commonly achieved using ultrasound guidance techniques, similar to traditional radial artery access via the wrist. After the procedure, the vascular access site is typically closed through application of pressure to encourage hemostasis.

Hemostatic devices that are wrapped around a patient's limb at a site on the limb where bleeding is to be stopped, and which include one or more inflatable balloons or bladders that target pressure at a vascular arterial access site, are known in the art. Multiple embodiments of one such hemostatic device and methods of using such devices are described in U.S. Pat. No. 7,498,477, the entirety of which is incorporated by reference as if set forth herein.

Such devices are commonly annular or cuff-like in shape, and when deployed on a patient's limb—especially a leg—may be prone to migration (i.e., movement), thus reducing the effectiveness of the device. A hemostatic device having a flexible element that is custom-shaped to fit around or conform to a particular body part or part(s) may be less prone to migration, thus representing an improvement over known devices.

Currently, a hemostatic closure device specific to the anatomy of the lower leg (e.g., ankle) and foot is not believed to exist. The present disclosure describes a new compression band that is specifically shaped to support patent hemostasis of the tibial arteries, namely the Dorsalis Pedis (DP) artery, Anterior Tibial (AT) artery, and Posterior Tibial (PT) artery.

Referring generally to FIGS. 1-9, one embodiment of a closure band 20 according to the above-noted inventive concept will be described in detail. As shown in FIGS. 3-9, in this embodiment the closure band 20 is designed to be wrapped and secured in place around portions of a lower leg 2 and foot 4 of a patient, the lower leg 2 comprising an ankle 3 and the foot 4 comprising a heel 5, bridge 6, and arch 7, as would be understood by a person having ordinary skill in the art.

In this embodiment, the closure band 20 comprises two half portions (not labeled) connected by a center seam 26. In alternate embodiments, the closure band 20 may be formed from a single piece of material or may be formed from more than two portions of material. In the present embodiment, the center seam 26 approximately corresponds with the underarch portion 28 of the closure device. As shown in the Figures, the arch 7 of the patient's foot 4 is placed atop the underarch portion 28 before the closure band 20 is wrapped around the foot 4.

Referring back to FIG. 1, the closure band 20 is shown in its undeployed or unwrapped state, lying flat on a planar surface. The closure band 20 has an interior side 22 that faces the lower leg 2 and foot 4 and an exterior side 24 (see FIG. 5) that faces away from the lower leg 2 and foot 4 when the closure band 20 is wrapped around the patient's lower leg 2 and foot 4. The closure band 20 comprises a strap 29 (see FIG. 6)—comprised of strap half 30 and strap half 34—which when assembled corresponds with a wrapped location seated around the posterior of the patient's ankle 3. The closure band 20 further comprises a strap 37 (see FIG. 5)—comprised of strap half 38 and strap half 42—which when assembled corresponds with a wrapped location seated around the anterior of the patient's ankle 3 and/or an upper portion of the bridge 6 of the patient's foot 4. The closure band 20 further comprises a strap 45 (see FIG. 5)—comprised of strap half 46 and strap half 50—which when assembled corresponds with a wrapped location seated around a lower portion of the bridge 6 of the patient's foot 4. In the present embodiment, each of the six strap halves 30,34,38,42,46,50 that comprise the three straps 29,37,45 includes a respective fastener half 32,36,40,44,48,52 that mates together with its respective complementary fastener half to form a respective completed fastener 31,39,49 (see FIGS. 4-6). Specifically, fastener half 32 of strap half 30 mates with fastener half 36 of strap half 34 to form completed fastener 31 of strap 29, fastener half 40 of strap half 38 mates with fastener half 44 of strap half 42 to form completed fastener 39 of strap 37, and fastener half 48 of strap half 46 mates with fastener half 52 of strap half 50 to form completed fastener 49 of strap 45. The strap 29 is adapted to fit around at least a portion of the lower leg 2 of a patient, and the straps 37,45 are adapted to fit around at least a portion of the foot 4 of the patient. The strap 29 may also be referred to as a "first strap," one of the straps 37,45 may also be referred to as a "second strap," and the other of the straps 37,45 may also be referred to as a "third strap." In this embodiment, the fasteners 31,39,49 include patches of hook-and-loop type fasteners (e.g., Velcro). In alternate embodiments, the fasteners could be formed from any suitable type of fastener, for example snaps, buttons, laces, zippers, or hook-and-eyelet combinations.

In this embodiment, an intermediate portion 54 is located to one side of the underarch portion 28 and an intermediate portion 60 is located to an opposite side of the underarch portion 28 of the closure band 20. Three strap halves 30,38,46 extend from the intermediate portion 54 and the other three strap halves 34,42,50 extend from the intermediate portion 60. Intermediate portion 54 comprises two additional fastener halves 56,58. As will be explained in greater detail below, fastener halves 56,58 are used to releasably attach a compression element 62 thereto that is used to supply targeted pressure to a desired vascular access site on the lower leg 2 or foot 4.

Figure 2:
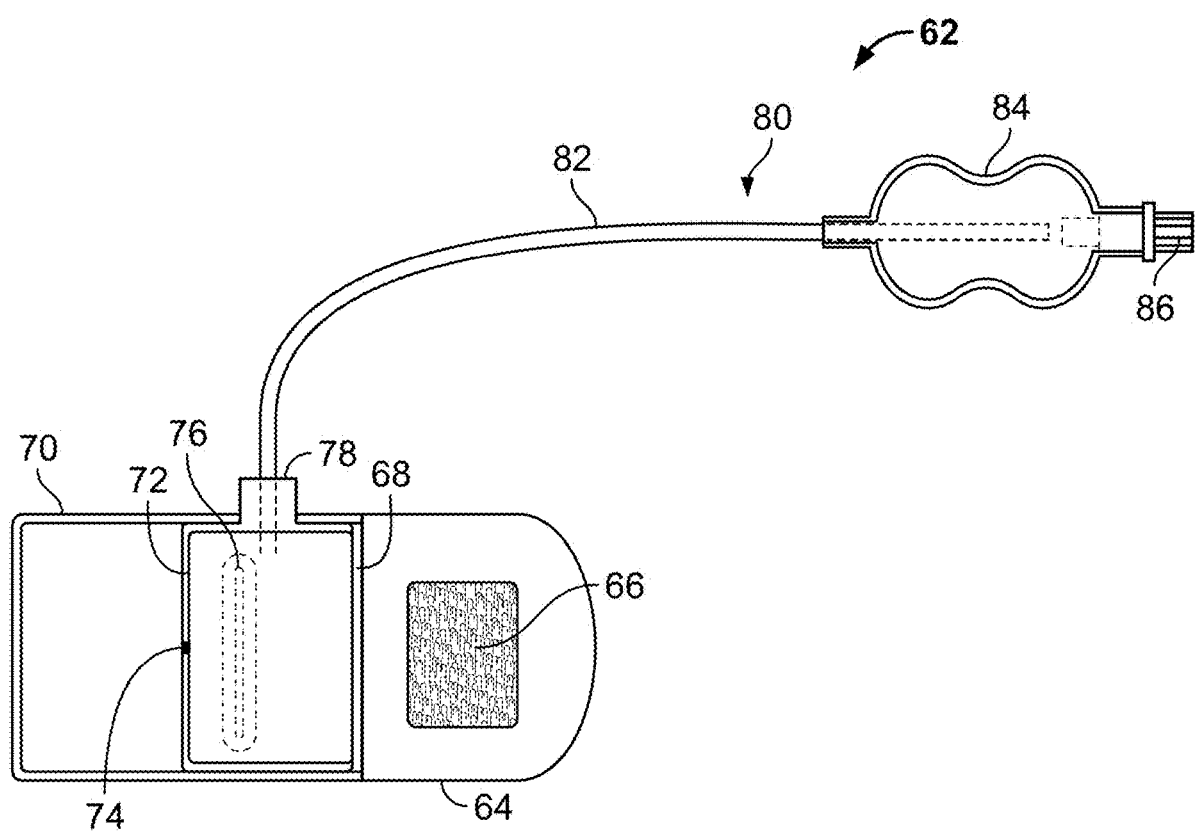
FIG. 2 is a front perspective view of a compression element according to an embodiment of the present disclosure, in an undeployed position separate from the closure band.
Figure 3:
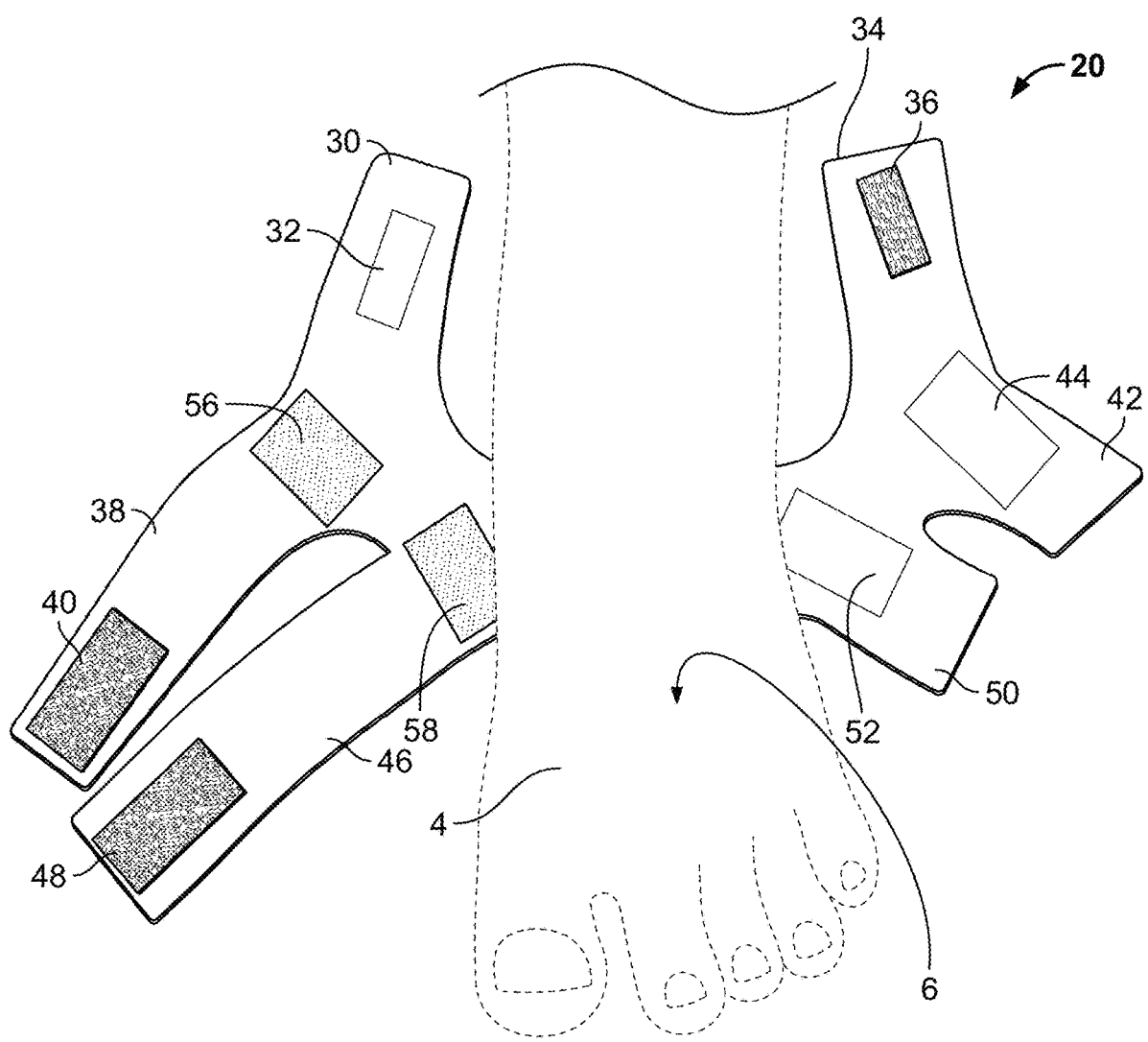
FIG. 3 is a front perspective view of the closure band of FIG. 1, with an exemplary lower leg and foot of a human patient shown placed over a portion thereof.

FIG. 2 shows the compression element 62, which in this embodiment is provided with an inflatable dual-balloon configuration similar to the embodiments taught in U.S. Pat. No. 7,498,477. The dual pneumatic balloon design supports a process to titrate air and reduce compression (pressure) during recovery, which allows for the artery or vein to remain patent over time. In this embodiment, the compression element 62 is comprised of a body 64 which includes a fastener half 66, a main balloon 70, a secondary balloon 72, and a connector 68 which serves as an intermediate joining portion between the body 64 and the main balloon 70 and secondary balloon 72. An opening 76 exists between an interior of the main balloon 70 and an interior of the secondary balloon 72, so that the secondary balloon 72 inflates as the main balloon 70 inflates, providing for efficient ease of use. A tube 82 enters the interior of the main balloon 70 via a port 78, and the tube 82 is connected at its opposite end to an inflator 80. The inflator 80 includes a bulb 84 and a connector 86. Inflation of the balloons 70,72 is achieved by inserting the protruding tip of a syringe (not shown) into the connector 86 and pushing a plunger on the syringe so as to introduce fluid (e.g., air) within the syringe through the inflator 80 into the balloons 70,72. Once fluid has been injected into the balloons 70,72 and the protruding tip of the syringe is withdrawn from the connector 86, a check valve (not shown) within the connector 86 closes, preventing the fluid from leaking out and thus maintaining the balloons 70,72 in an inflated state. In the present embodiment, when both balloons 70,72 are inflated, the secondary balloon 72 provides oblique pressure against the main balloon 70, which in turn provides targeted pressure to the respective artery or vein, thus promoting hemostasis.

In this embodiment, the compression element 62 further includes a marker 74 located on an interior edge of the secondary balloon 72 (and approximately in the center of the main balloon 70), which permits the clinician to align the balloons 70,72 over the center of the vascular access site. In alternate embodiments, the marker 74 could be omitted.

In additional alternate embodiments, the compression element 62 could be formed with only one balloon and/or balloon(s) of different sizes than the balloons 70,72 of the present embodiment. In further alternate embodiments the balloons could be omitted entirely, and the hemostatic pressure could be achieved via a material pad or a mechanical device that applies targeted pressure to the desired vascular access site.

In the present embodiment, both the closure band 20 and the compression element 62 are transparent to allow for visualization of the vascular access site and monitor for bleeding during the hemostasis period. Further, in the present embodiment, the closure band 20 is comprised of polyvinyl chloride (PVC). In alternate embodiments, all or portions of the closure band 20 and/or compression element 62 could be formed from opaque materials and/or alternate types of materials. In further alternate embodiments, only the portions of the closure band 20 that are to be located in the vicinity of the tibial vascular access sites could be formed from transparent materials, and the remainder of the closure band 20 could be formed from opaque and/or semi-opaque materials. The closure band 20 could also optionally be equipped with a patency monitoring sensor.

In the present embodiment, the fastener half 66 permits the compression element 62 to be releasably attached to either of the fastener halves 56,58 located on the intermediate portion 54 of the closure band 20. Since the balloons 70,72 of the compression element 62 are located offset from the fastener half 66 thereof, and the fastener halves 56,58 of the closure band 20 are located away from the arterial access sites 10,12,14, the balloons 70,72 of the compression element 62 can be deployed atop of a selected one of the arterial access sites 10,12,14 without interfering with said respective arterial access site 10,12,14. In this embodiment, the fastener halves 56,58,66 comprise patches of hook-and-loop type fasteners (e.g., Velcro). In alternate embodiments, these fastener halves could be formed from any suitable type of fastener, for example snaps, buttons, laces, zippers, or hook-and-eyelet combinations. In further alternate embodiments, one or more balloons could be integrated into the one or more strap halves 30,34,38,42,46,50, negating the need for the compression element 62 to be a separate unit and for the fastener halves 56,58 entirely.

The locations of the fastener halves 56,58 and the dimensions of the body 64 of the compression element 62 have been carefully selected to permit the compression element 62 to be attached to the different fastener halves 56,58 and oriented in different directions so that the balloons 70,72 are located above one of the selected three arterial access sites—namely the Dorsalis Pedis (DP) arterial access site 10, the Anterior Tibial (AT) arterial access site 12, and the Posterior Tibial (PT) arterial access site 14. In alternate embodiments, the closure band 20 could be equipped with additional fastener halves that permit for multiple compression elements to be attached to the closure band 20 at once, for example where dual tibial or tibiopedal access occurs during a procedure.

Figure 4:
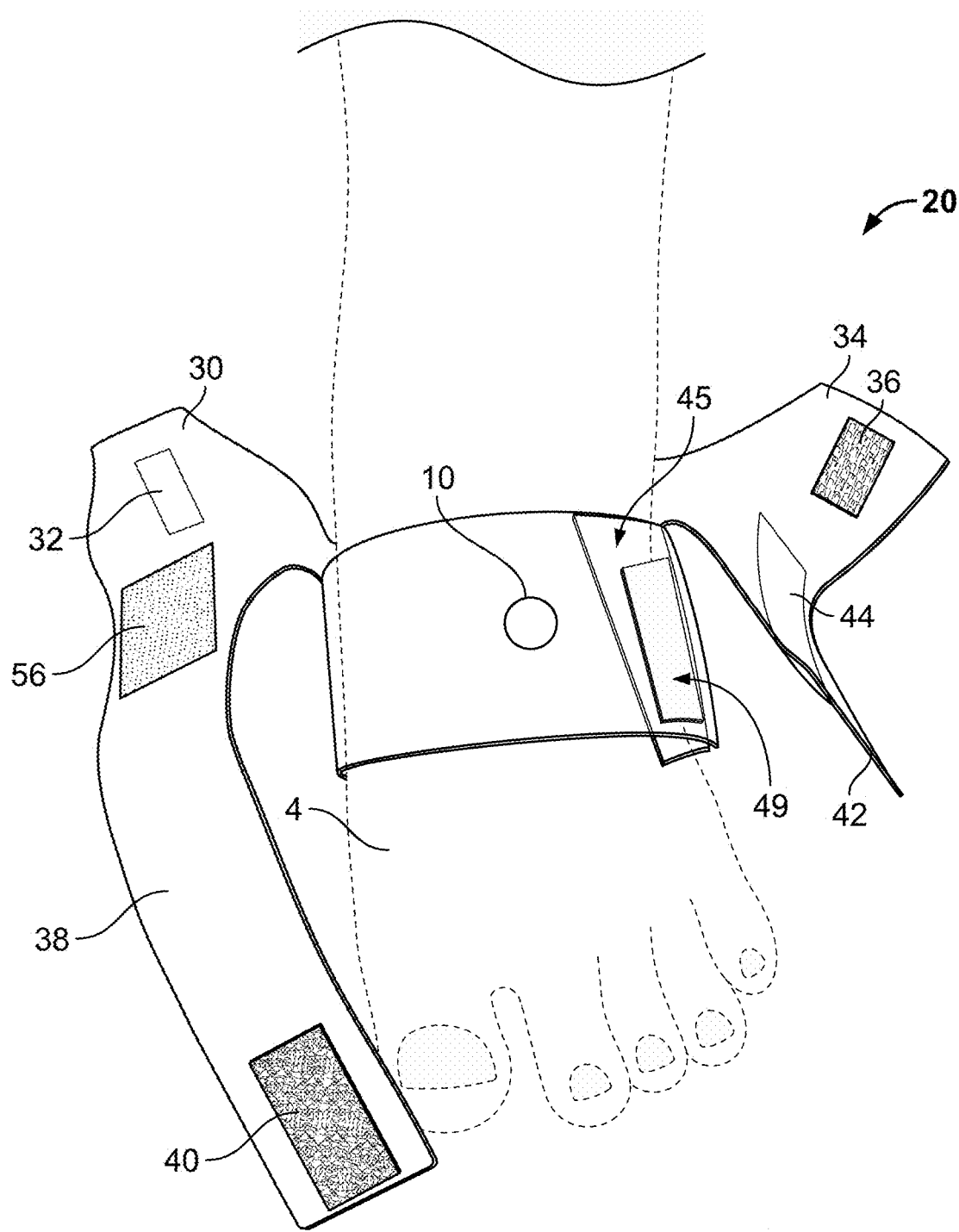
FIG. 4 is a front perspective view thereof, with the closure band shown in a partially-wrapped configuration.
Figure 9:
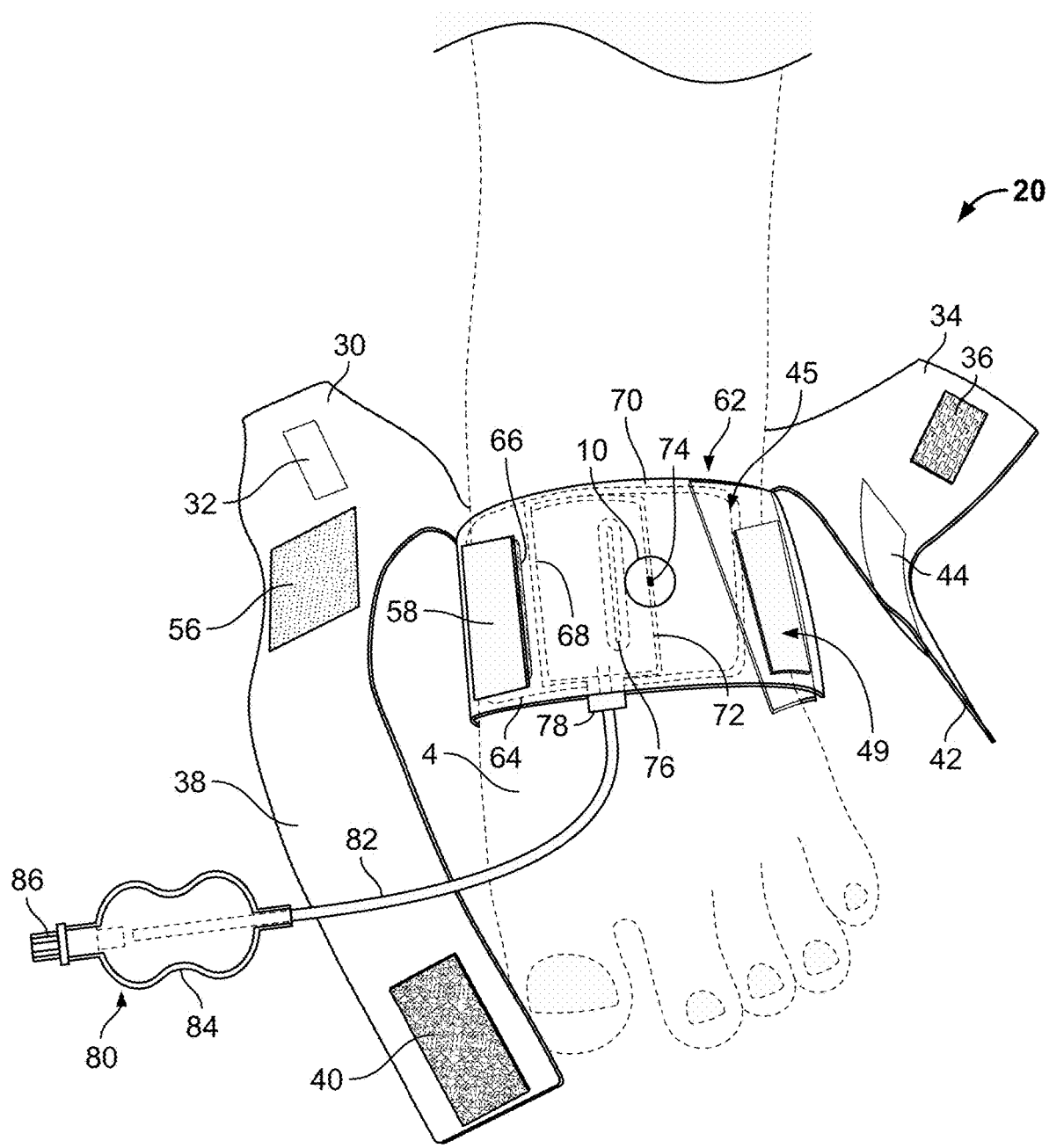
FIG. 9 is a front perspective view of the closure band of FIG. 1, with the compression element according to FIG. 2 in a third deployed position attached to the closure band.

Turning back to the present embodiment, FIG. 4 shows the completed strap 45 wrapped around the bridge 6 of the patient's foot 4, located atop the DP arterial access site 10. As shown in FIG. 9, where the DP arterial access site 10 is used for a procedure and hemostatic pressure needs to be supplied at this site 10, the fastener half 66 of the compression element 62 is attached to the fastener half 58 and the remainder of the compression element 62 is run up the bridge 6 of the foot 4 so that the balloons 70,72 of the compression element 62 are placed underneath the strap 45, atop the DP arterial access site 10. The compression element 62 is then inflated, as discussed above. When the compression element 62 is located atop the DP arterial access site 10, it is possible—as shown in FIG. 9—for the straps 29,37 to not be attached around the patient's ankle 3 and the bridge 6 of the patient's foot 4, or these straps 29,37 could be wrapped therearound to help hold the closure band 20 and compression element 62 in place during the hemostasis period.

Figure 5:
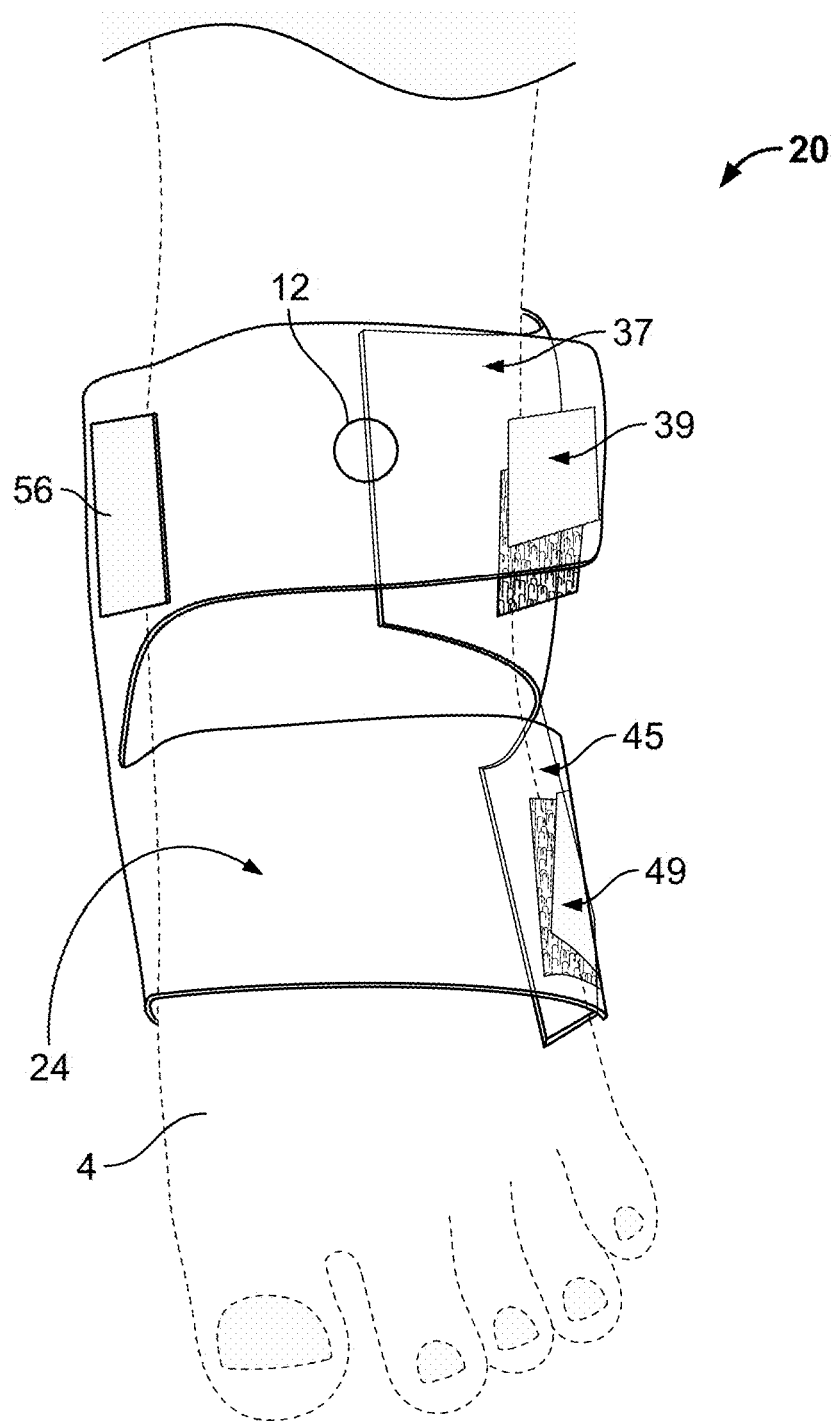
FIG. 5 is a front perspective view thereof, with the closure band shown in a fully-wrapped configuration located around the patient's lower leg and foot.
Figure 6:
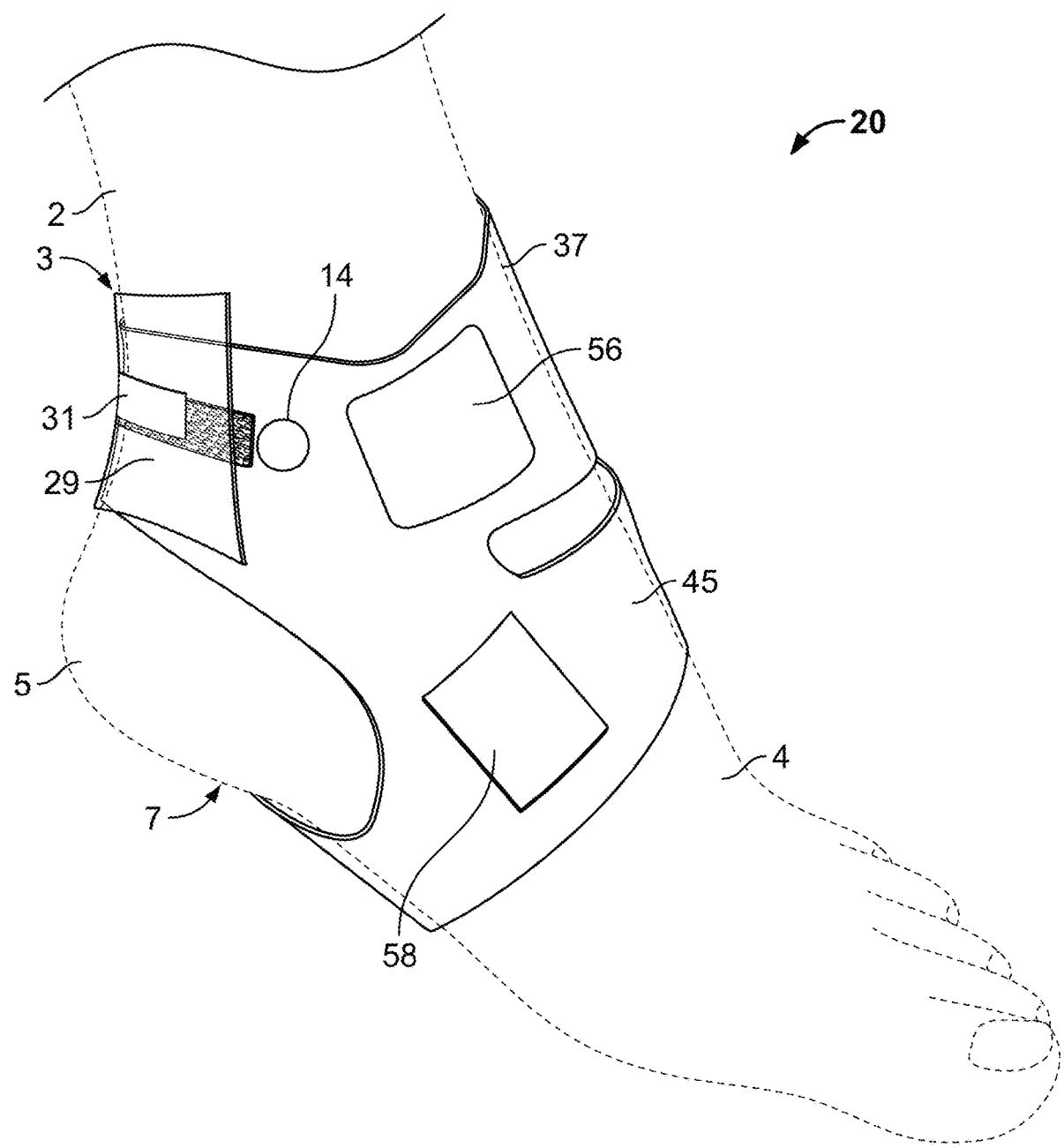
FIG. 6 is a perspective side view thereof.
Figure 7:
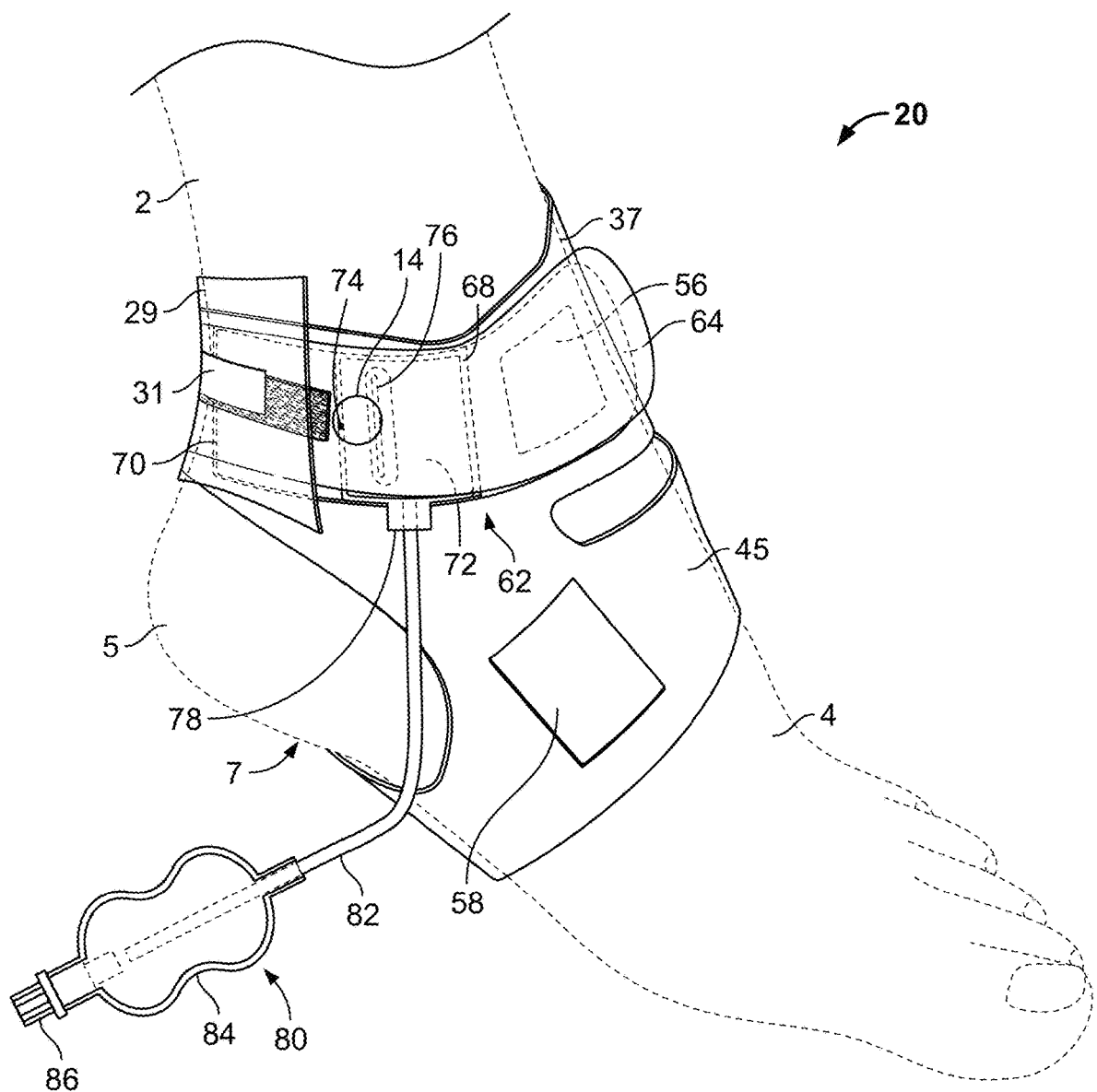
FIG. 7 is a perspective side view thereof, with a compression element according to FIG. 2 in a first deployed position attached to the closure band.
Figure 8:
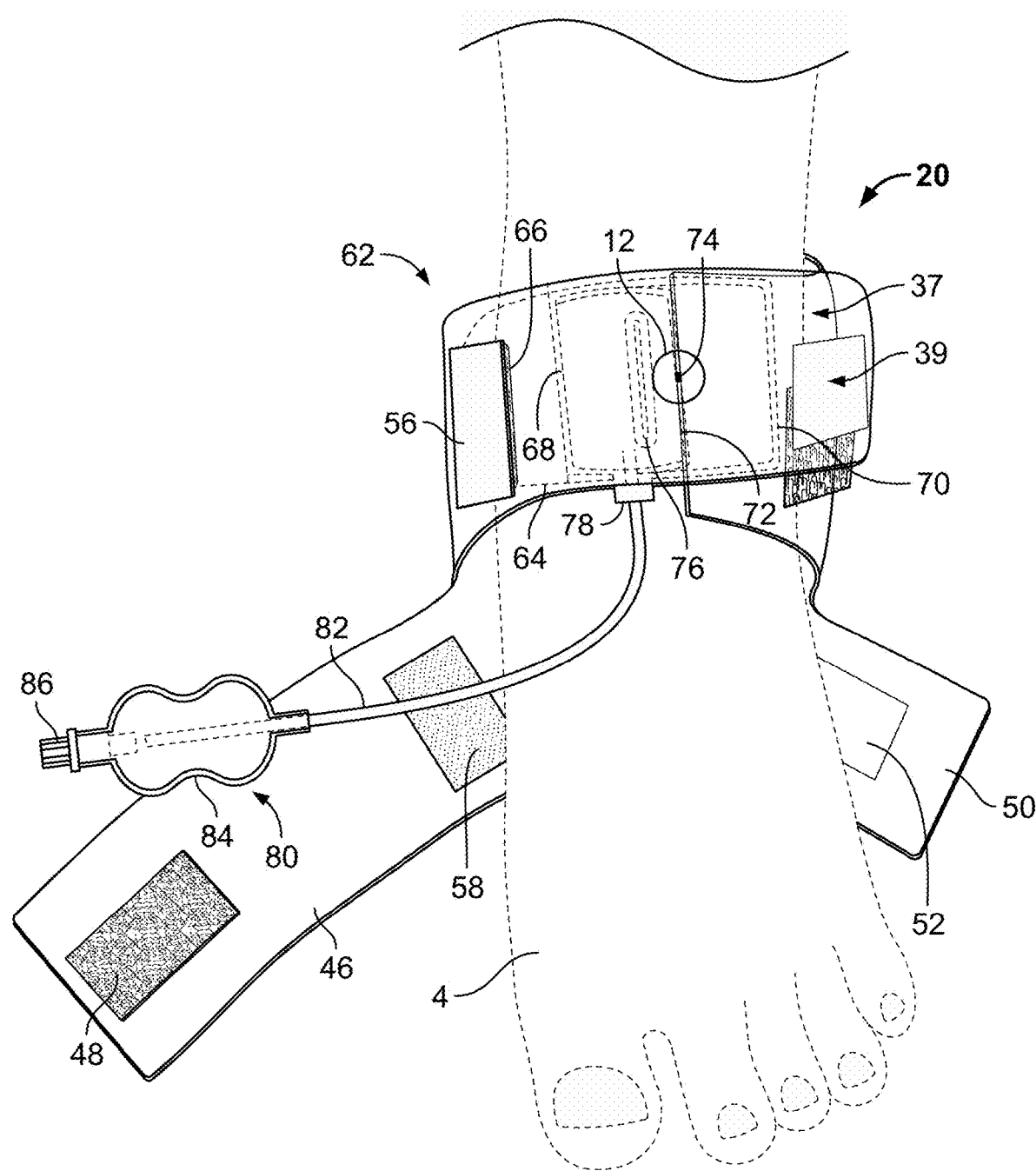
FIG. 8 is a front perspective view of the closure band of FIG. 1, with the compression element according to FIG. 2 in a second deployed position attached to the closure band.

FIGS. 5 and 6 show the completed straps 29,37 wrapped around the ankle 3 and upper portion of the bridge 6 of the patient's foot 4. The completed straps 29,37 are located atop the AT arterial access site 12 and PT arterial access site 14. FIGS. 7-9 show views of the compression element 62 according to FIG. 2, attached to the closure band 20 in various deployed positions. As shown in FIG. 8, where the AT arterial access site 12 is used for a procedure and hemostatic pressure needs to be supplied at this site 12, the fastener half 66 of the compression element 62 is attached to the fastener half 56 and the remainder of the compression element 62 is run up the bridge 6 of the foot 4 (i.e., to the anterior side of the foot 4) so that the balloons 70,72 of the compression element 62 are placed underneath the strap 37, atop the AT arterial access site 12. The compression element 62 is then inflated, as discussed above. As further shown in FIG. 8, when the compression element 62 is located atop the AT arterial access site 12 or PT arterial access site 14, it is possible for the strap 45 to not be attached around the patient's foot 4, or the strap 45 could be wrapped therearound to help hold the closure band 20 and compression element 62 in place during the hemostasis period.

As shown in FIG. 7, where the PT arterial access site 14 is used for a procedure and hemostatic pressure needs to be supplied at this site 14, the fastener half 66 of the compression element 62 is attached to the fastener half 56 and the remainder of the compression element 62 is run around the ankle 3 (i.e., towards the lateral side of the foot 4) so that the balloons 70,72 of the compression element 62 are placed underneath the strap 29 atop the PT arterial access site 14. The compression element 62 is then inflated, as discussed above. When the compression element 62 is located atop the AT arterial access site 12 or PT arterial access site 14, it is possible for the strap 45 to not be attached around the patient's foot 4, or the strap 45 could be wrapped therearound to help hold the closure band 20 and compression element 62 in place during the hemostasis period.

The inventors have used anthropometric data for the foot and ankle of a group of humans to select the optimal dimension and angles of the straps so that the closure band 20 according to the present disclosure can be used on a range of patients having variations in foot and ankle shapes and sizes. Nonetheless, the inventors have determined that it may be desirable to produce the closure band 20 in different sizes (e.g., small, medium, and large) and with minor variations in the angles of the straps to better accommodate an appropriate percentage of the spectrum of variation in human foot and ankle size. For example, it may be desirable to produce various closure bands according to the present disclosure that are suitable to fit all humans within three, four, five, or six standard deviations from mean human foot and ankle size, or all humans falling within a certain range of percentiles for foot and ankle size, for example the $5^{th}$-$95^{th}$ percentiles or $2^{nd}$-$98^{th}$ percentiles. In further alternate embodiments, the closure band 20 may be shaped and sized in left and right foot versions, based on collected anthropometric data.

While the principles of the claimed invention have been described above in connection with specific embodiment(s), it is to be clearly understood that this description is made only by way of example and not as a limitation of the scope of the invention, as set forth in the appended claims.

The invention claimed is:

1. A closure device adapted to simultaneously fit around at least a portion of a lower leg and at least a portion of a foot of a patient, the lower leg having an ankle, the closure device comprising:
   a first strap that fits around the at least a portion of the lower leg of the patient;
   a second strap that fits around the at least a portion of the foot of the patient;
   at least one compression element adapted to apply targeted pressure to at least one artery or vein located in at least one of the lower leg and foot at a location on the ankle or foot of the patient, the targeted pressure having a value that substantially exceeds the value of standard forces that are applied to the remainder of the lower leg and foot via attachment of the first strap around the at least a portion of the lower leg of the patient and attachment of the second strap around the at least a portion of the foot of the patient;
   at least one attachment element, the at least one attachment element adapted for either fixed or removeable attachment of the at least one compression element thereto such that at least a portion of the compression element is located between the first strap and the patient's ankle or foot or between the second strap and the patient's ankle or foot.

2. The closure device of claim 1, wherein the closure device is adjustable to fit around at least a portion of a lower leg and at least a portion of a foot of a plurality of patients, each of the plurality of patients having a lower leg or foot of differing size or shape.

3. The closure device of claim 1, wherein the at least one compression element comprises at least one inflatable element.

4. The closure device of claim 3, wherein the at least one compression element comprises a plurality of inflatable elements.

5. The closure device of claim 4, wherein the plurality of inflatable elements comprises at least two inflatable balloons that press into each other when inflated to assist in the application of the targeted pressure to the at least one artery or vein.

6. The closure device of claim 1, further comprising a third strap that fits around at least an additional portion of the patient's lower leg or foot.

7. The closure device of claim 1, wherein the at least one attachment element is a first attachment element and the closure device further comprises a second attachment element, wherein both the first attachment element and the second attachment element are adapted for removeable attachment of the at least one compression element thereto such that at least a portion of the at least one compression element is located between the first strap and the patient's ankle or foot or between the second strap and the patient's ankle or foot.

8. The closure device of claim 7, wherein the at least one compression element is removably attachable to either the first attachment element or the second attachment element to permit selective application of the targeted pressure to one of the patient's *dorsalis* pedis artery, anterior tibial artery, and posterior tibial artery.

9. The closure device of claim 1, wherein at least a portion of the closure device is transparent.

10. The closure device of claim 1, further comprising a patency monitoring sensor attached thereto.

11. A hemostatic device comprising:
    a flexible element adapted to be wrapped and releasably secured around at least a portion of a lower leg and at least a portion of a foot of a patient, the lower leg having an ankle, the flexible element comprising a first strap that fits around the at least a portion of the lower leg of the patient and a second strap that first around the at least a portion of the foot of the patient;
    at least one compression element adapted to apply targeted pressure to at least one artery or vein located in at least one of the lower leg and foot at a location on the ankle or foot of the patient, the at least one compression element being fixedly attached or removably attachable to the flexible element, the targeted pressure having a value that substantially exceeds the value of standard forces that are applied to the remainder of the lower leg and foot via attachment of the first strap around the at least a portion of the lower leg of the patient and attachment of the second strap around the at least a portion of the foot of the patient; and
    at least one attachment element that is used to attach the at least one compression element to the flexible element such that at least a portion of the at least one compression element is located between the first strap and the patient's ankle or foot or between the second strap and the patient's ankle or foot.

12. The hemostatic device of claim 11, wherein the first strap, when fitted around the at least a portion of the lower leg of the patient, is located atop an access site for the anterior tibial artery located on the ankle of the patient.

13. The hemostatic device of claim 11, the flexible element having an interior side that abuts the at least a portion of the lower leg and the at least a portion of the foot when wrapped and releasably secured around the at least a portion of the lower leg and the at least a portion of the foot of the patient, wherein at least a portion of the at least one compression element is located between the interior side and the at least a portion of the lower leg or the at least a portion of the foot of the patient.

14. The hemostatic device of claim 11, wherein the flexible element further comprises a third strap that fits around at least an additional portion of the patient's lower leg or foot.

15. The hemostatic device of claim 11, wherein the at least one attachment element is a first attachment element and the hemostatic device further comprises a second attachment element, wherein both the first attachment element and the second attachment element are adapted for removeable attachment of the at least one compression element thereto such that at least a portion of the at least one compression element is located between the first strap and the patient's ankle or foot or between the second strap and the patient's ankle or foot.

16. The hemostatic device of claim 15, wherein the at least one compression element is removably attachable to either the first attachment element or the second attachment element to permit selective application of the targeted pressure to one of the patient's *dorsalis* pedis artery, anterior tibial artery, and posterior tibial artery.

17. A method of forming a closure device, the method comprising:

forming the closure device with a first portion that is adapted to be wrapped and releasably secured around at least a portion of a lower leg of a patient, the lower leg having an ankle;

forming the closure device with a second portion that is adapted to be wrapped and releasably secured around at least a portion of a foot of the patient;

providing the closure device with at least one attachment element, the at least one attachment element adapted for either fixed or removeable attachment of at least one compression element thereto, the at least one compression element adapted to apply targeted pressure to at least one artery or vein located in at least one of the lower leg and foot at a location on the ankle or foot of the patient, the targeted pressure having a value that substantially exceeds the value of standard forces that are applied to the remainder of the lower leg and foot via attachment of the first portion around the at least a portion of the lower leg of the patient and attachment of the second portion around the at least a portion of the foot of the patient.

18. The method of claim 17, further comprising forming the closure device with a third portion that is adapted to be wrapped and releasably secured around at least one additional portion of the patient's lower leg or foot.

19. The method of claim 18, wherein the step of providing the closure device with at least one attachment element further comprises providing the closure device with a second attachment element, wherein both the first attachment element and the second attachment element are adapted for removeable attachment of the at least one compression element thereto.

20. The closure device of claim 1, wherein the first strap, when fitted around the at least a portion of the lower leg of the patient, is located atop an access site for the anterior tibial artery located on the ankle of the patient.

* * * * *